(12) United States Patent
Lewis

(10) Patent No.: US 11,571,117 B2
(45) Date of Patent: Feb. 7, 2023

(54) APPARATUS AND METHODS FOR LUBRICATING DEVICES INTRODUCED INTO A BODY OF A PATIENT

(71) Applicant: Dennis Lewis, Horseshoe Beach, FL (US)

(72) Inventor: Dennis Lewis, Horseshoe Beach, FL (US)

(*) Notice: Subject to any disclaimer, the term of this patent is extended or adjusted under 35 U.S.C. 154(b) by 800 days.

(21) Appl. No.: 16/503,384

(22) Filed: Jul. 3, 2019

(65) Prior Publication Data

US 2020/0008664 A1 Jan. 9, 2020

Related U.S. Application Data

(60) Provisional application No. 62/693,974, filed on Jul. 4, 2018.

(51) Int. Cl.
*A61M 31/00* (2006.01)
*A61B 1/31* (2006.01)

(52) U.S. Cl.
CPC .............. *A61B 1/31* (2013.01); *A61M 31/00* (2013.01); *A61M 2205/0216* (2013.01); *A61M 2210/1064* (2013.01)

(58) Field of Classification Search
CPC ......... A61B 1/31; A61B 1/00131; A61B 1/12; A61M 31/00; A61M 2205/0216; A61M 2210/1064; A61M 2025/0213; A61M 2025/0253; A61M 25/02; A61M 2205/0222; A61M 2025/0062; A61M 25/01; A61M 25/0111; A61M 39/0247
See application file for complete search history.

(56) References Cited

U.S. PATENT DOCUMENTS

| | | | |
|---|---|---|---|
| 5,242,428 A * | 9/1993 | Palestrant | A61M 25/01 604/265 |
| 5,368,574 A * | 11/1994 | Antonacci | A61M 39/0606 604/167.02 |
| 2008/0051630 A1* | 2/2008 | Levey | A61B 1/12 600/114 |
| 2015/0328437 A1* | 11/2015 | Rageh | A61F 5/449 604/540 |
| 2016/0339205 A1* | 11/2016 | Foley | A61M 25/0043 |
| 2019/0262583 A1* | 8/2019 | Her | A61M 25/02 |

* cited by examiner

*Primary Examiner* — Bhisma Mehta
*Assistant Examiner* — Phoebe Anne Staton
(74) *Attorney, Agent, or Firm* — William A. English; Vista IP Law Group LLP

(57) ABSTRACT

Apparatus and methods are provided for lubricating a medical device, such as a colonoscope, being introduced into a patient's body. In one embodiment, the apparatus includes a housing including a proximal surface, a distal surface, a channel extending between the proximal and distal surfaces; and a lubricant within an interior of the housing surrounding the channel such that a scope or other device inserted through the channel receives lubricant on its outer surface before introduction into a patient's body.

23 Claims, 3 Drawing Sheets

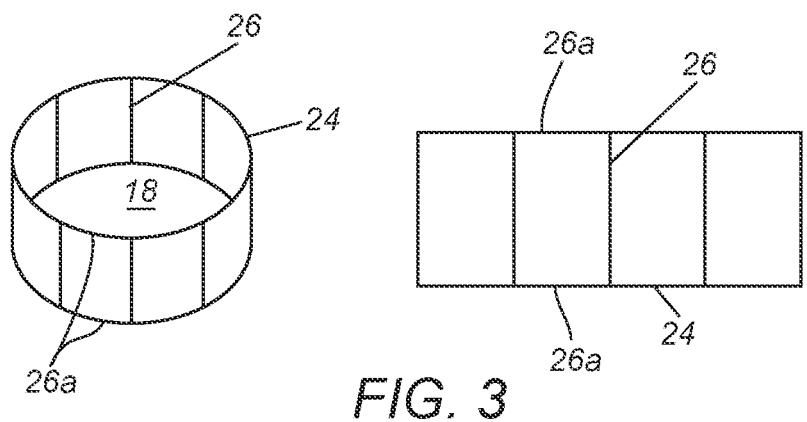
FIG. 3
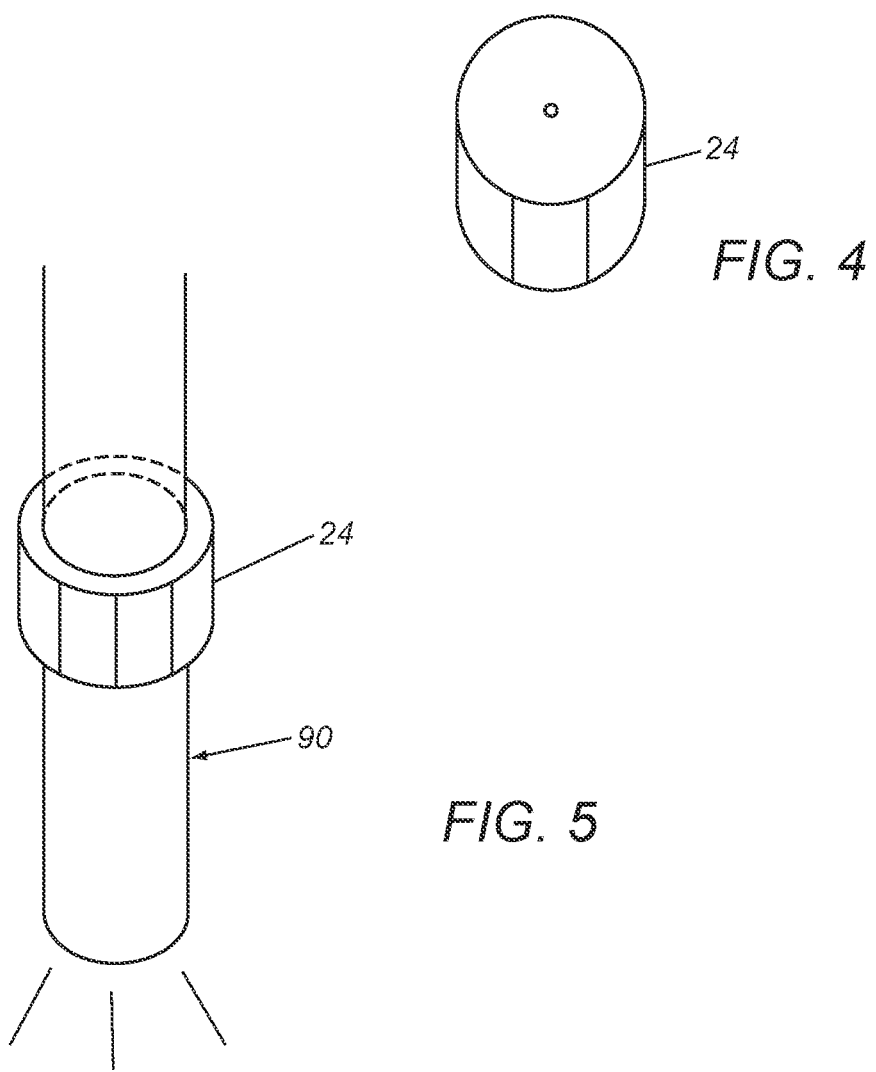
FIG. 4
FIG. 5

APPARATUS AND METHODS FOR LUBRICATING DEVICES INTRODUCED INTO A BODY OF A PATIENT

RELATED APPLICATION DATA

The present application claims benefit of U.S. provisional application Ser. No. 62/693,974, filed Jul. 4, 2018, the entire disclosure of which is expressly incorporated by reference herein.

FIELD OF THE INVENTION

The present invention relates to apparatus and methods for facilitating introduction of devices into a patient's body, e.g., for automatically lubricating colonoscopes, endoscopes, or other elongate devices during introduction through the rectum into the colon or other natural orifice and/or body lumens.

BACKGROUND

During endoscopic procedures, a colonoscope, endoscope, or other device may be inserted through the rectum into a patient's colon, e.g., to acquire images and/or perform a medical procedure within the patient's gastrointestinal tract. To facilitate insertion, lubricant, e.g., water-based jelly, petroleum jelly, or other lubricant, may be applied to the distal end of the device and/or to the patient's body around the rectum. However, such manual application may be messy and/or result in uneven application of the lubricant and may require the user to then wash and/or otherwise clean their hands to allow subsequent manipulation of the endoscope and completion of the procedure.

Accordingly, apparatus and methods for facilitating application of lubricant would be useful.

SUMMARY

The present invention is directed to apparatus and methods for facilitating introduction of devices into a patient's body, e.g., for automatically lubricating colonoscopes, endoscopes, and/or other elongate devices during introduction through the rectum into the colon or other natural orifice and/or body lumens.

In accordance with one embodiment, an apparatus is provided for lubricating a medical device being introduced into a patient's body that includes a housing including a proximal surface, a distal surface, a channel extending between the proximal and distal surfaces; and a lubricant within an interior of the housing surrounding the channel such that a device inserted through the channel receives lubricant on its outer surface before introduction into a patient's body.

In accordance with another embodiment, a method is provided for introducing a medical device into a body passage of a patient's body that includes providing a lubricant apparatus including lubricant within an interior surrounding a channel through the apparatus; introducing a distal end of a medical device into and through the channel, whereupon lubricant from the interior is applied to an outer surface of the medical device; and introducing the distal end of the medical device into the body passage to perform a procedure, lubricant being applied to the outer surface of the medical device as the medical device passes through the channel and into the body passage.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which:

FIG. 3 shows a perspective view and a side view of a ring that may be provided around the channel of the apparatus of FIGS. 1 and 2 to automatically deliver lubricant to the outer surface of a device inserted through the channel.

FIGS. 4 and 5 show a colonoscope being inserted through the ring of FIG. 3.

DETAILED DESCRIPTION OF THE EXEMPLARY EMBODIMENTS

Figure 1:
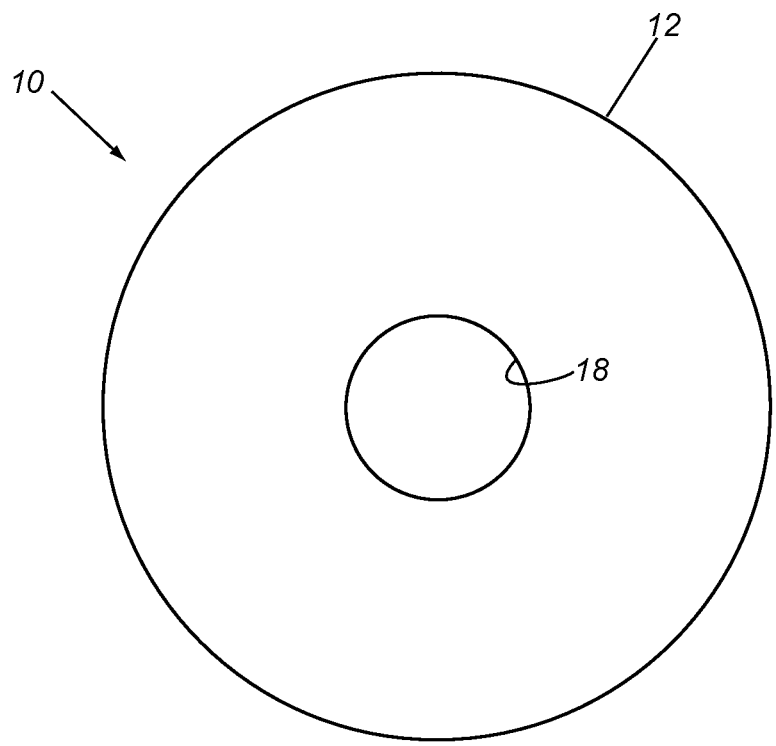
FIGS. 1 and 2 are end and cross-sectional side views, respectively, of an example of a lubricating apparatus for applying lubricant to a medical device inserted through a channel in the apparatus.
Figure 2:
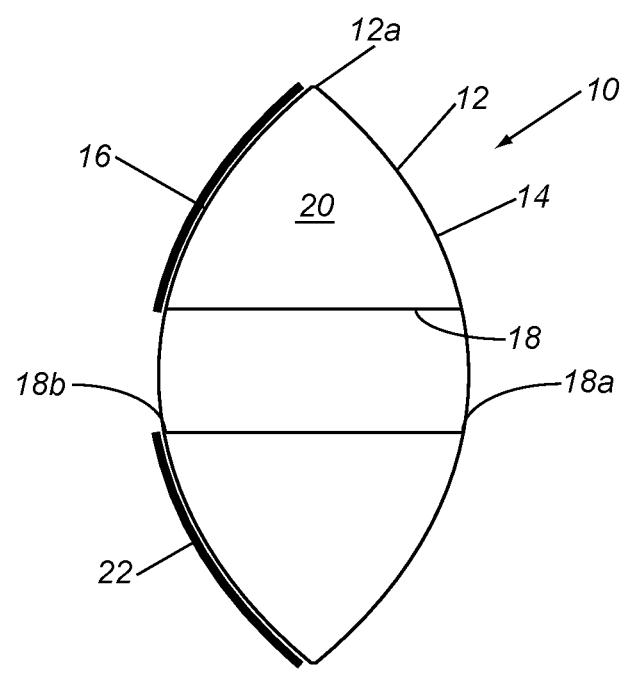

Turning to the drawings, FIGS. 1 and 2 show an exemplary embodiment of a lubricating apparatus 10 or "jelly donut" device that includes an outer housing 12 including proximal and distal surfaces 14, 16, and a channel 18 extending between the surfaces 14, 16, e.g., from openings 18a, 18b. The housing 12 defines an inner annular chamber 20 surrounding the channel 18 that may be filled with lubricant, e.g., water-based lubricant, such as K-Y jelly, petroleum jelly, and the like.

As shown, the housing 12 may define an annular or "donut" shape, e.g., with the surfaces 14, 16 tapering from the channel 18 to an outer edge 12a defining an outer circumference for the housing 12. Optionally, the housing 12 may have other desired shapes, e.g., a distal surface 16 shaped to conforms to the patient's skin or other anatomy against which the apparatus 10 may be positioned (not shown), e.g., having a substantially flat, convex, concave, or other shape that may conform to the patient's anatomy. As shown, the surfaces 14, 16 may taper outwardly such they meet at the outer edge 12a, although alternatively, the surfaces may define a rounded outer edge and/or other shape (not shown).

In addition, the distal surface 16 may include an adhesive or other tacky material 22 that may cover all or a portion of the distal surface 16, e.g., at least around the outer edge 12a, immediately around the distal channel opening 18b, and the like, to facilitate anchoring and/or stabilizing the apparatus 10 against a patient's body, e.g., over the rectum (not shown). For example, the material 22 may be sufficiently tacky to secure the distal surface 16 to the patient's skin during a procedure, yet be removable upon completion of the procedure while leaving little or no residue on the patient's skin.

In one embodiment, the housing 12 may be formed from a flexible and/or elastic material, e.g., plastic material having sufficient strength to contain the lubricant within the interior 20 yet being sufficiently flexible, e.g., to minimize risk of damage and/or to conform partially to the patient's skin or other contacted body. For example, the proximal surface 14 and/or distal surface 16 may include a flexible elastic cover with a hole or opening 18a, 18b in the center. One or both of the surfaces 14, 16 may be biased to a predetermined shape, yet the material may be flexible to conform to the patient's anatomy, e.g., such that the distal surface 16 may be deflected or deformed to be seated against the patient's skin.

Before use, e.g., when packaged and/or manufactured, the opening(s) 18a, 18b may be covered, e.g., with a removable sheet, cover, or other sealing member (not shown) to prevent the lubricant within the interior 20 from escaping from the apparatus 10. Alternatively, an annular cover (also not shown) may be provided that extends along the channel 18 to prevent lubricant from leaking from the chamber 20. The cover may be slid out of the channel 18 or may be peeled, torn, or otherwise removed before use to expose the channel 18 to the lubricant.

Optionally, the proximal opening 18a may include an annular taper, ramp, bell-mouth and/or the like (not shown) to facilitate guiding a device being inserted into the channel 18.

In the example shown in FIGS. 3-5, the channel 18 may be defined by a ring 24 extending between the proximal and distal openings 18a, 18b in the proximal and distal surfaces 14, 16. The ring 24 may include one or more openings, e.g., between a plurality of ribs or other scaffold structure, to allow lubricant within the interior 20 to enter the channel 18. For example, as shown in FIG. 3, the ring 24 may include a plurality of struts or longitudinal elements 26 that extend longitudinally along the channel 18, e.g., between the proximal and distal surfaces (not shown in FIG. 3). Optionally, the ring 24 may include one or more annular struts, webbing, and/or other structures, e.g., two annular elements 26a shown in FIG. 3, to define a channel 18 of the apparatus 10 yet provide openings for the lubricant within the interior 20 to enter the channel 18.

In one embodiment, the ring 24 may be sufficiently rigid to define a substantially fixed diameter, e.g., having a diameter slightly larger than the diameter of an colonoscope or other device 90 (shown in FIG. 5) that may be introduced through the channel 18, e.g., greater than 10-13 mm. Alternatively, the ring 24 may be formed from elastic material to allow the ring 24 to expand to accommodate different size devices being inserted through the channel 18 yet providing a close fit, e.g., to provide a partial seal around the device 90 to prevent leakage of the lubricant, particularly through the opening 18a in the proximal surface 14.

In another embodiment, the ring 24 may be replaced by an annular wall that includes a plurality of openings or pores having cross-sections sufficiently large to allow lubricant to pass through the wall into the channel 18 at a desired rate, while preventing excessive lubricant from escaping. Optionally, the openings may include valve elements, e.g., individual flaps formed in the wall or attached over the openings (not shown), which may open when a device is directed though the channel 18 to deliver lubricant, yet may close when nothing is in the channel 18 to prevent the lubricant from leaking. In another option, the wall may be formed from permeable material that has pores sufficiently large to allow the lubricant to pass through the wall into the channel 18.

The openings and/or pores may be evenly distributed around the perimeter and/or length of the wall. Alternatively, the openings or pores may be provided only along a portion of the channel 18, e.g., from the proximal surface 14 only partially along the length of the channel 18 towards the distal surface 16.

When ready to use, any cover or sealing member may be removed to uncover the opening(s) 18a, 18b and/or the distal surface 16, and a distal end of a colonoscope or other device 90 may be inserted through the proximal opening 18a in the proximal surface 14 (i.e., the endoscopist or user side) into the channel 18, which, optionally, may stretch to facilitate passage of the scope 90 into the channel 18. Optionally, the ring 24 and/or housing 18 may be formed from elastic material that provides a close elastic fit around the scope 90, e.g., to remove excess lubricant when the scope 90 exits the channel 18 through the distal opening 18b.

If the distal surface 16 (i.e., patient side of the channel 18) includes a removable, e.g., annular, cover (not shown) over the adhesive 22, the cover may be removed before or after inserting the scope 90 through the channel. The distal opening 18b may be slightly larger than the scope 90 (e.g., greater than 10-13 mm diameter) to allow the lubricant to stay on the outer surface of the scope 90 and/or provide a squeegee to apply a desired thickness of lubricant on the outer surface as the scope 90 passes into the patient, e.g., into the rectum.

After initial insertion through the channel 18, the scope 90 may be introduced into the patient's body, e.g., through the rectum into the colon (not shown). The apparatus 10 may then be seated against the patient, e.g., thereby pressing the distal surface 16 against the patient's skin surrounding the rectum, which may apply the adhesive to the skin to prevent the apparatus 10 from moving during manipulation of the scope 90. Alternatively, the distal surface 16 of the apparatus 10 may be placed against the patient's skin, e.g., with the channel 18 aligned with the rectum, before introducing the scope 90.

With the apparatus 10 shown in FIGS. 1 and 2, as the scope 90 is advanced, lubricant may be automatically applied to the outer surface of the scope 90 as it passes through the channel 10, thereby facilitating advancement of the scope 90 into the patient's colon. The scope 90 may then be used to perform a procedure, e.g., observing and/or treating the patient's colon. Upon completing the procedure, the scope 90 may be removed, and then the apparatus 10 may be removed. Optionally, one more additional instruments may be introduced through the channel 18 before removing the apparatus 10.

Figure 6:
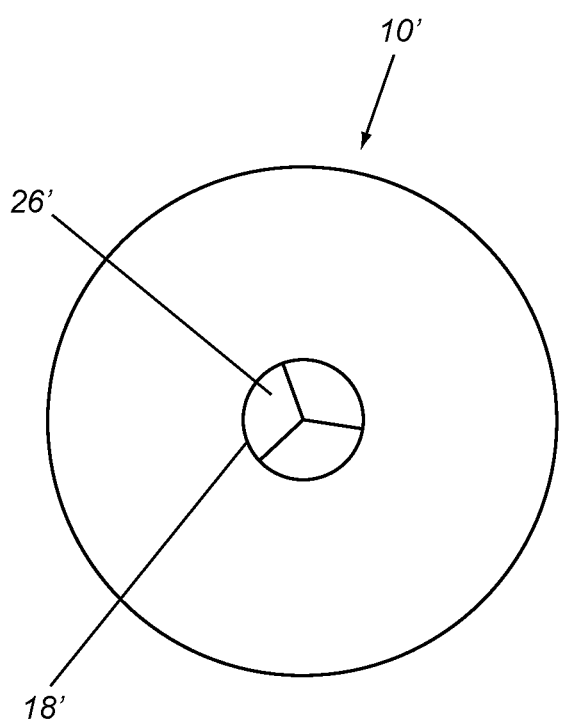
FIGS. 6 and 7 are end and side views, respectively, of another example of a lubricating apparatus.
Figure 7:
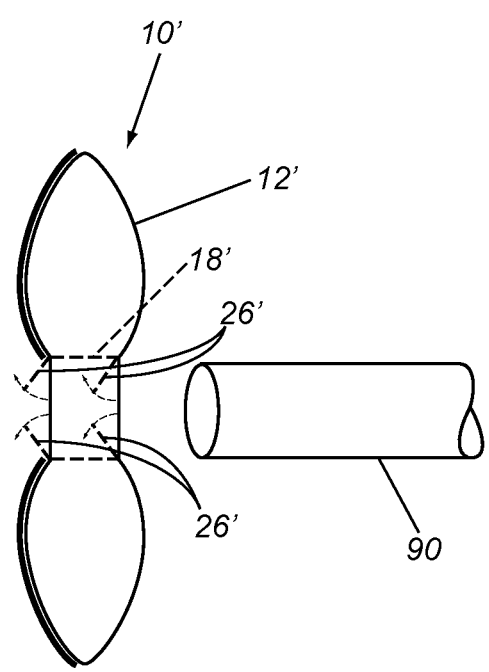

Alternatively, as shown in FIGS. 6 and 7, a lubricating apparatus 10' may be provided that is constructed generally similar to the previous embodiment, e.g., including a housing 12' having a channel 18' therethrough. In this alternative, one-way valves 26 may be provided that surround and/or seal the proximal and distal openings 18a', 18b' communicating with the channel 18'. The valves 26 may be biased to closed positions but may be movable to open positions to allow insertion of a scope or other device 90 into and through the channel 18' with the scope 90 receiving lubricant within the housing 12' on its outer surface as it passes through the channel 18', similar to the previous embodiments. Upon completion of the procedure, the scope 90 may be removed from the colon through the channel 18,' whereupon the valves 26 may automatically close as the apparatus 10 is removed.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

I claim:

1. An apparatus for lubricating a medical device being introduced into a rectum of a patient's body, comprising:

a housing including a proximal surface including a proximal opening, a distal surface including a distal opening, a channel extending between the proximal and distal openings, wherein the distal surface surrounds the distal opening to define a distal-most surface of the housing such that the distal surface is configured to be placed against the patient around the rectum;

adhesive or tacky material on the distal surface surrounding the distal opening to secure the distal surface to the patient around the rectum; and a lubricant within an interior of the housing such that the medical device inserted through the channel receives the lubricant on an outer surface thereof before introduction into the patient's body, wherein the lubricant comprises one of water-based jelly and petroleum jelly.

2. The apparatus of claim 1, wherein the housing comprises an annular wall surrounding the channel.

3. The apparatus of claim 2, wherein the annular wall comprises permeable material that allows the lubricant from the interior of the housing to pass through the annular wall into the channel to apply the lubricant to the medical device inserted through the channel.

4. The apparatus of claim 2, wherein the annular wall comprises a plurality of openings therethrough sized to allow the lubricant from the interior of the housing to pass through the annular wall into the channel to apply the lubricant to the medical device inserted through the channel.

5. The apparatus of claim 2, wherein the annular wall is formed from elastic material such that the annular wall may expand to accommodate different size devices being inserted through the channel.

6. The apparatus of claim 1, wherein the housing is formed from elastic material such that the channel may expand to accommodate different size devices being inserted through the channel.

7. The apparatus of claim 1, wherein the housing comprises an annular ring surrounding the channel, the annular ring comprising a plurality of annular elements extending around the channel and a plurality of longitudinal elements extending between the proximal surface and the distal surface.

8. The apparatus of claim 1, further comprising valve members covering one or both of the proximal and distal openings, wherein the valve members are biased closed but open to accommodate inserting the medical device through the channel.

9. The apparatus of claim 1, further comprising a removable cover overlying the adhesive or tacky material.

10. The apparatus of claim 1, further comprising a removable seal covering one of the proximal and distal openings.

11. The apparatus of claim 1, further comprising a removable seal extending through the channel for preventing the lubricant from escaping from the interior of the housing until the removable seal is removed.

12. The apparatus of claim 1, wherein the distal surface is formed from a cover extending outwardly from the distal opening.

13. The apparatus of claim 12, wherein the cover is formed from flexible material configured to conform to the patient's body around the rectum.

14. The apparatus of claim 1, wherein the interior of the housing extends between the proximal and distal surfaces and the lubricant fills the interior between the proximal and distal surfaces.

15. The apparatus of claim 1, further comprising a valve member in each of the proximal and distal openings that are biased to closed positions to prevent lubricant from leaking from the interior but movable to open positions to allow insertion of the medical device into and through the channel.

16. A method for introducing a medical device into a body passage of a patient's body, comprising:

providing a lubricant apparatus including a proximal surface including a proximal opening, a distal surface including a distal opening, a channel communicating with the proximal and distal openings, and including lubricant within an interior of the lubricant apparatus;

introducing a distal end of a medical device into and through the channel, whereupon lubricant from the interior of the lubricant apparatus is applied to an outer surface of the medical device;

placing the distal surface against the patient's skin around the body passage, the distal surface comprising adhesive or tacky material surrounding the distal opening to secure the distal surface around a rectum; and introducing the distal end of the medical device into the body passage to perform a procedure, such that at least some of the lubricant is applied to the outer surface of the medical device as the medical device passes through the channel and into the body passage.

17. The method of claim 16, wherein the medical device is a scope and the body passage is a rectum communicating with the patient's colon.

18. The method of claim 16, wherein the distal end of the medical device is introduced through the channel before introducing the distal end of the medical device into the body passage.

19. The method of claim 18, wherein the distal surface is placed against the patient's skin after introducing the distal end of the medical device into the body passage.

20. The method of claim 16, further comprising:

removing the medical device entirely from the body passage; and removing the lubricant apparatus.

21. The method of claim 16, wherein providing the lubricant apparatus comprises removing one or more covers from the lubricant apparatus before introducing the distal end of the medical device into and through the channel.

22. The method of claim 21, wherein the one or more covers comprise a cover on each of the proximal opening and the distal opening.

23. The method of claim 16, wherein the lubricant comprises one of water-based jelly and petroleum jelly.

* * * * *